US008679172B2

(12) United States Patent
Dorn et al.

(10) Patent No.: US 8,679,172 B2
(45) Date of Patent: Mar. 25, 2014

(54) DELIVERY DEVICE FOR DELIVERING A STENT DEVICE

(75) Inventors: Jürgen Dorn, Neulussheim (DE); Beate Walter, Stutensee (DE)

(73) Assignee: C. R. Bard, Inc., Murray Hill, NJ (US)

( * ) Notice: Subject to any disclaimer, the term of this patent is extended or adjusted under 35 U.S.C. 154(b) by 79 days.

(21) Appl. No.: 13/147,120

(22) PCT Filed: Jan. 27, 2010

(86) PCT No.: PCT/EP2010/050910
§ 371 (c)(1),
(2), (4) Date: Jul. 29, 2011

(87) PCT Pub. No.: WO2010/086320
PCT Pub. Date: Aug. 5, 2010

(65) Prior Publication Data
US 2012/0059449 A1   Mar. 8, 2012

Related U.S. Application Data

(60) Provisional application No. 61/148,188, filed on Jan. 29, 2009.

(30) Foreign Application Priority Data

Jan. 29, 2009   (GB) .................................. 0901496.0

(51) Int. Cl.
*A61F 2/84*   (2006.01)
(52) U.S. Cl.
USPC ........................................................ 623/1.12

(58) Field of Classification Search
USPC ............... 623/1.11, 1.12, 1.13, 903; 606/108, 606/194, 198
See application file for complete search history.

(56) References Cited

U.S. PATENT DOCUMENTS

| 4,576,534 A | 3/1986 | Barth et al. |
| 4,580,568 A | 4/1986 | Gianturco |
| 4,719,853 A | 1/1988 | Bowers |
| 4,762,128 A | 8/1988 | Rosenbluth |

(Continued)

FOREIGN PATENT DOCUMENTS

| CA | 2537366 A1 | 4/2005 |
| DE | 10016920 A1 | 10/2001 |

(Continued)

OTHER PUBLICATIONS

CA 2,523,557 filed Apr. 28, 2004 Offical Action dated Aug. 20, 2010.

(Continued)

*Primary Examiner* — Elizabeth Houston
(74) *Attorney, Agent, or Firm* — Rutan & Tucker, LLP

(57) ABSTRACT

A delivery device (12) for delivering a stent device (3) in a reduced profiled delivery configuration is provided. A distal region (9) of the stent device is axially anchored to an inner catheter (2) by annular rings (5, 6) about the inner catheter. A remaining portion (10) of the stent device is spaced radially from the inner catheter. A proximal stop (4) is spaced axially from a proximal end of the stent device. The stent device is maintained in the reduced profile delivery configuration by a retractable outer sheath (1).

20 Claims, 1 Drawing Sheet

(56) References Cited

U.S. PATENT DOCUMENTS

| | | |
|---|---|---|
| 4,768,507 A | 9/1988 | Fischell et al. |
| 4,950,227 A | 8/1990 | Savin et al. |
| 5,026,377 A | 6/1991 | Burton et al. |
| 5,037,427 A | 8/1991 | Harada et al. |
| 5,201,757 A | 4/1993 | Heyn et al. |
| 5,201,901 A | 4/1993 | Harada et al. |
| 5,445,646 A | 8/1995 | Euteneuer et al. |
| 5,458,605 A | 10/1995 | Klemm |
| 5,474,563 A | 12/1995 | Myler et al. |
| 5,480,423 A | 1/1996 | Ravenscroft et al. |
| 5,484,444 A | 1/1996 | Braunschweiler et al. |
| 5,520,645 A | 5/1996 | Imran et al. |
| 5,554,181 A | 9/1996 | Das |
| 5,562,641 A | 10/1996 | Flomenblit et al. |
| 5,562,726 A | 10/1996 | Chuter |
| 5,569,295 A | 10/1996 | Lam |
| 5,569,296 A | 10/1996 | Marin et al. |
| 5,591,222 A | 1/1997 | Susawa et al. |
| 5,609,627 A | 3/1997 | Goicoechea et al. |
| 5,619,878 A | 4/1997 | Grosjean et al. |
| 5,645,559 A | 7/1997 | Hachtman et al. |
| 5,683,451 A | 11/1997 | Lenker et al. |
| 5,697,948 A | 12/1997 | Marin et al. |
| 5,700,269 A | 12/1997 | Pinchuk et al. |
| 5,702,418 A | 12/1997 | Ravenscroft |
| 5,709,703 A | 1/1998 | Lukic et al. |
| 5,749,880 A | 5/1998 | Banas et al. |
| 5,749,921 A | 5/1998 | Lenker et al. |
| 5,755,777 A | 5/1998 | Chuter |
| 5,776,141 A | 7/1998 | Klein et al. |
| 5,807,327 A | 9/1998 | Green et al. |
| 5,824,040 A | 10/1998 | Cox et al. |
| 5,824,041 A | 10/1998 | Lenker et al. |
| 5,843,167 A | 12/1998 | Dwyer et al. |
| 5,876,448 A | 3/1999 | Thompson et al. |
| 5,902,334 A | 5/1999 | Dwyer et al. |
| 5,913,871 A | 6/1999 | Werneth et al. |
| 5,920,975 A | 7/1999 | Morales |
| 5,928,258 A | 7/1999 | Khan et al. |
| 5,968,068 A | 10/1999 | Dehdashtian et al. |
| 5,980,532 A | 11/1999 | Wang |
| 5,980,548 A | 11/1999 | Evans et al. |
| 5,989,280 A | 11/1999 | Euteneuer et al. |
| 6,033,388 A | 3/2000 | Nordstrom et al. |
| 6,048,350 A | 4/2000 | Vrba |
| 6,056,906 A | 5/2000 | Werneth et al. |
| 6,063,092 A | 5/2000 | Shin |
| 6,077,295 A | 6/2000 | Limon et al. |
| 6,110,142 A | 8/2000 | Pinchuk et al. |
| 6,110,180 A | 8/2000 | Foreman et al. |
| 6,110,191 A | 8/2000 | Dehdashtian et al. |
| 6,113,628 A | 9/2000 | Borghi et al. |
| 6,132,458 A | 10/2000 | Staehle et al. |
| 6,143,014 A | 11/2000 | Dehdashtian et al. |
| 6,203,568 B1 | 3/2001 | Lombardi et al. |
| 6,210,429 B1 | 4/2001 | Vardi et al. |
| 6,214,039 B1 | 4/2001 | Banas et al. |
| 6,245,099 B1 | 6/2001 | Edwin et al. |
| 6,258,099 B1 | 7/2001 | Mareiro et al. |
| 6,302,893 B1 | 10/2001 | Limon et al. |
| 6,302,906 B1 | 10/2001 | Goicoechea et al. |
| 6,306,162 B1 | 10/2001 | Patel |
| 6,319,275 B1 | 11/2001 | Lashinski et al. |
| 6,322,586 B1 | 11/2001 | Monroe et al. |
| 6,352,531 B1 | 3/2002 | O'Connor et al. |
| 6,451,047 B2 | 9/2002 | McCrea et al. |
| 6,471,718 B1 | 10/2002 | Staehle et al. |
| 6,500,202 B1 | 12/2002 | Shaolian et al. |
| 6,576,006 B2 | 6/2003 | Limon et al. |
| 6,607,551 B1 | 8/2003 | Sullivan et al. |
| 6,613,075 B1 | 9/2003 | Healy et al. |
| 6,620,172 B1 | 9/2003 | Dretler et al. |
| 6,620,191 B1 | 9/2003 | Svensson |
| 6,758,858 B2 | 7/2004 | McCrea et al. |
| 6,776,791 B1 | 8/2004 | Stallings et al. |
| 6,796,998 B2 | 9/2004 | Schaldach et al. |
| 6,858,034 B1 | 2/2005 | Hijlkema et al. |
| 6,945,989 B1 | 9/2005 | Betelia et al. |
| 7,011,675 B2 | 3/2006 | Hemerick et al. |
| 7,172,618 B2 | 2/2007 | Lupton |
| 7,241,308 B2 | 7/2007 | Andreas et al. |
| 7,473,271 B2 | 1/2009 | Gunderson |
| 7,717,949 B2 | 5/2010 | Dorn |
| 7,867,267 B2 | 1/2011 | Sullivan et al. |
| 8,287,582 B2 | 10/2012 | Dorn |
| 2001/0001833 A1 | 5/2001 | Ravenscroft et al. |
| 2001/0032009 A1 | 10/2001 | Layne et al. |
| 2001/0039446 A1 | 11/2001 | Edwin et al. |
| 2001/0049549 A1 | 12/2001 | Boylan et al. |
| 2002/0029076 A1 | 3/2002 | Yee |
| 2002/0038143 A1 | 3/2002 | McCrea et al. |
| 2002/0058993 A1 | 5/2002 | Landau et al. |
| 2002/0138966 A1 | 10/2002 | Motsenbocker |
| 2002/0147490 A1 | 10/2002 | Pletzer et al. |
| 2002/0156516 A1 | 10/2002 | Vardi et al. |
| 2002/0193863 A1 | 12/2002 | Rourke et al. |
| 2003/0032999 A1 | 2/2003 | Huang |
| 2003/0153969 A1 | 8/2003 | Dehdashtian et al. |
| 2004/0106977 A1 | 6/2004 | Sullivan et al. |
| 2004/0143272 A1 | 7/2004 | Cully et al. |
| 2004/0204749 A1 | 10/2004 | Gunderson |
| 2006/0184225 A1 | 8/2006 | Pryor |
| 2006/0184226 A1 | 8/2006 | Austin |
| 2006/0216404 A1 | 9/2006 | Seyler et al. |
| 2006/0259123 A1 | 11/2006 | Dorn |
| 2006/0276873 A1 | 12/2006 | Sato |
| 2007/0024072 A1 | 2/2007 | Leon |
| 2007/0043430 A1 | 2/2007 | Stinson |
| 2007/0083256 A1 | 4/2007 | Dorn |
| 2007/0156251 A1 | 7/2007 | Karmon |
| 2007/0191925 A1* | 8/2007 | Dorn ............................ 623/1.12 |
| 2008/0051867 A1 | 2/2008 | Davila et al. |
| 2009/0177264 A1 | 7/2009 | Ravenscroft |
| 2010/0070016 A1 | 3/2010 | Dorn et al. |
| 2012/0143304 A1 | 6/2012 | Wubbeling et al. |
| 2013/0079863 A1 | 3/2013 | Dorn |

FOREIGN PATENT DOCUMENTS

| | | |
|---|---|---|
| DE | 10212707 A1 | 10/2003 |
| DE | 20306823 U1 | 11/2003 |
| EP | 0596145 A1 | 5/1994 |
| EP | 0775470 A1 | 5/1997 |
| EP | 0788332 | 8/1997 |
| EP | 0826346 | 3/1998 |
| EP | 0834293 A1 | 4/1998 |
| EP | 0836447 A2 | 4/1998 |
| EP | 0873731 | 10/1998 |
| EP | 0943300 A1 | 9/1999 |
| EP | 1382367 A1 | 1/2004 |
| EP | 1466570 A1 | 10/2004 |
| EP | 1803423 A3 | 6/2009 |
| FR | 2742042 A1 | 6/1997 |
| FR | 2760351 A1 | 9/1998 |
| JP | 08-141090 A | 6/1996 |
| JP | 11-512318 T | 10/1999 |
| JP | 2001-501115 A | 1/2001 |
| JP | 2002-501404 A | 1/2002 |
| JP | 2003-500103 A | 1/2003 |
| JP | 2003-500104 A | 1/2003 |
| JP | 2005-038367 A | 2/2005 |
| JP | 2007-024072 A | 2/2007 |
| JP | 2008-508937 A | 3/2008 |
| WO | 9533422 A1 | 12/1995 |
| WO | 9628115 A1 | 9/1996 |
| WO | 9639998 A2 | 12/1996 |
| WO | 9709932 A1 | 3/1997 |
| WO | 9814233 A1 | 4/1998 |
| WO | 9831305 A1 | 7/1998 |
| WO | 9853761 A1 | 12/1998 |
| WO | 9955255 | 11/1999 |
| WO | 0012030 A9 | 10/2000 |
| WO | 0071057 A1 | 11/2000 |
| WO | 0071058 A1 | 11/2000 |

(56) References Cited

FOREIGN PATENT DOCUMENTS

| WO | 0105331 | | 1/2001 |
|---|---|---|---|
| WO | 0121103 | A2 | 3/2001 |
| WO | 0134061 | A1 | 5/2001 |
| WO | 0215820 | A2 | 2/2002 |
| WO | 03003944 | A2 | 1/2003 |
| WO | 03024362 | A1 | 3/2003 |
| WO | 03049641 | A1 | 6/2003 |
| WO | 2004062458 | A2 | 7/2004 |
| WO | 2004096091 | A1 | 11/2004 |
| WO | 2004096091 | A8 | 3/2005 |
| WO | 2004110521 | A3 | 3/2005 |
| WO | 2005030092 | A3 | 7/2005 |
| WO | 2005053574 | A3 | 2/2006 |
| WO | 2006020028 | A1 | 2/2006 |
| WO | 2006026377 | A1 | 3/2006 |
| WO | 2007149464 | A2 | 12/2007 |
| WO | 2009033066 | A1 | 3/2009 |
| WO | 2010136558 | A1 | 12/2010 |

OTHER PUBLICATIONS

GB 0901496.0 Search Report dated Apr. 28, 2009.
JP 2006-505303 filed Feb. 16, 2006 Office Action dated Mar. 23, 2010.
JP 2006-527350 Examination Report (translated) dated Aug. 6, 2009.
PCT/EP2004/004486 filed Apr. 28, 2004 International Preliminary Report on Patentability dated Oct. 28, 2005.
PCT/EP2004/004486 filed Apr. 28, 2004 Search Report dated Sep. 27, 2004.
PCT/EP2004/004486 filed Apr. 28, 2004 Written Opinion dated Sep. 27, 2004.
PCT/EP2009/061918 filed Sep. 5, 2009 Search Report dated Nov. 25, 2009.
PCT/EP2009/061918 filed Sep. 15, 2009 Written Opinion dated Nov. 25, 2009.
PCT/EP2010/050910 filed Jan. 27, 2010 International Preliminary Report on Patentability dated Aug. 2, 2011 and Written Opinion dated Mar. 30, 2010.
PCT/EP2010/050910 filed Jan. 27, 2010 International Search Report dated Mar. 30, 2010.
PCT/EP2010/057401 filed May 28, 2010 International Preliminary Report on Patentability dated Sep. 16, 2011.
PCT/EP2010/057401 filed May 28, 2010 International Search Report dated Aug. 9, 2010.
PCT/EP2010/057401 filed May 28, 2010 Written Opinion dated Aug. 9, 2010.
PCT/US2000/014038 filed May 19, 2000 International Preliminary Examination Report dated Jul. 31, 2001.
PCT/US2000/014038 filed May 19, 2000 Search Report dated Sep. 13, 2000.
U.S. Appl. No. 10/552,886, filed Nov. 18, 2005 Non-Final Office Action dated Sep. 28, 2007.
U.S. Appl. No. 10/552,886, filed Nov. 18, 2005 Final Office Action dated Oct. 29, 2008.
U.S. Appl. No. 10/552,886, filed Nov. 18, 2005 Non-Final Office Action dated Apr. 2, 2008.
U.S. Appl. No. 10/552,886, filed Nov. 18, 2005 Non-Final Office Action dated Sep. 8, 2007.
U.S. Appl. No. 10/552,886, filed Nov. 18, 2005 Decision on Appeal dated Jan. 11, 2012.
U.S. Appl. No. 10/552,886, filed Nov. 18, 2005 Notice of Allowance dated May 18, 2012.
U.S. Appl. No. 10/572,191, filed Apr. 11, 2006 Advisory Action dated Jan. 2, 2009.
U.S. Appl. No. 10/572,191, filed Apr. 11, 2006 Final Office Action dated Jun. 8, 2009.
U.S. Appl. No. 10/572,191, filed Apr. 11, 2006 Final Office Action dated Oct. 10, 2008.
U.S. Appl. No. 10/572,191, filed Apr. 11, 2006 Final Office Action dated Oct. 5, 2009.
U.S. Appl. No. 10/572,191, filed Apr. 11, 2006 Non-Final Office Action dated Mar. 25, 2008.
U.S. Appl. No. 12/560,295, filed Sep. 15, 2009 Non-Final Office Action dated Oct. 26, 2012.
U.S. Appl. No. 12/560,295, filed Sep. 15, 2009 Final Office Action dated Feb. 15, 2013.
JP 2011-546827 Office Action (translated) dated Sep. 20, 2013.

\* cited by examiner

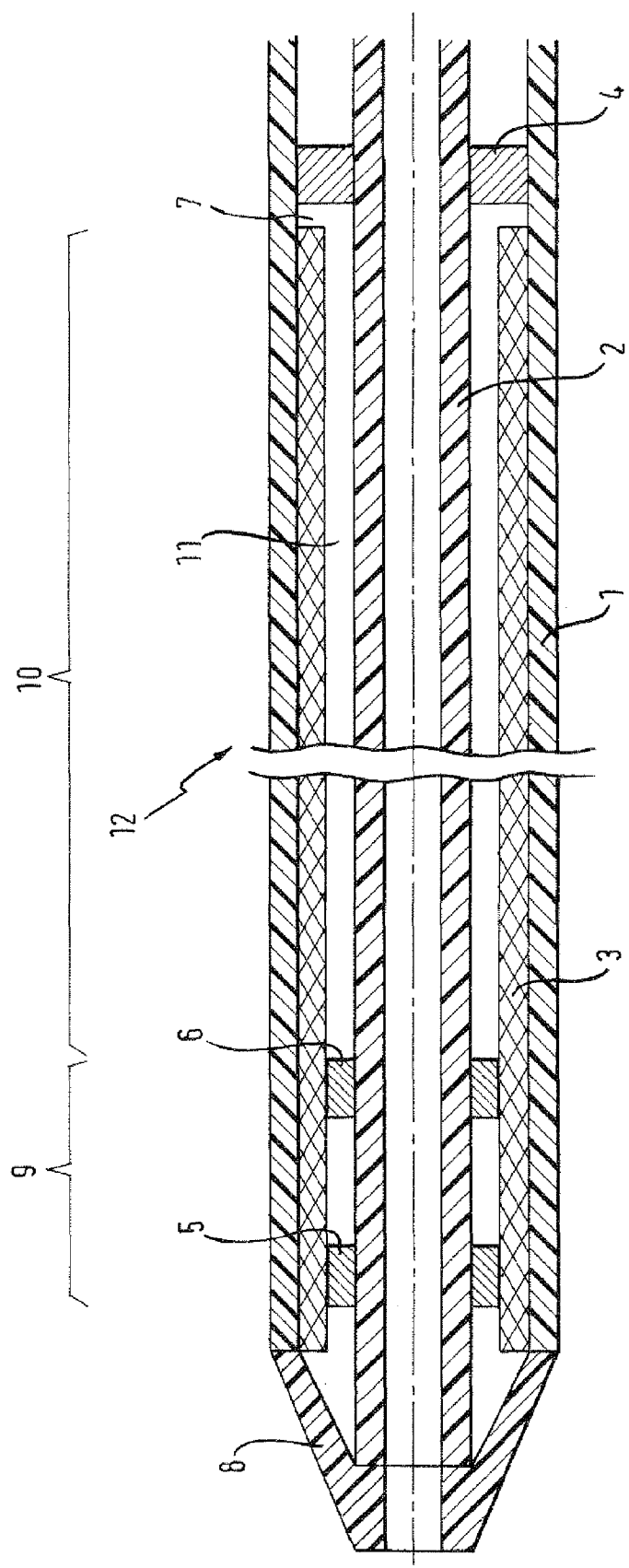

DELIVERY DEVICE FOR DELIVERING A STENT DEVICE

PRIORITY

This application is a U.S. national stage application under 35 USC §371 of International Application No. PCT/EP2010/050910, filed Jan. 27, 2010, claiming priority to United Kingdom Patent Application No. 0901496.0, filed Jan. 29, 2009, and to U.S. Provisional Application No. 61/148,188, filed Jan. 29, 2009, each of which is incorporated by reference in its entirety into this application.

FIELD OF THE INVENTION

The present invention is concerned with a delivery device for delivering a stent device to a target site. The delivery device includes an outer sheath for maintaining the stent device in a reduced profile delivery configuration. The stent device is held on an inner catheter extending through a lumen of the stent device. The outer sheath may be retracted as the stent device is held on the inner catheter so as to release the stent device to radially expand to a deployed configuration.

BACKGROUND OF THE INVENTION

Stent devices are useful for holding open bodily lumens of a human or animal patient. Of particular interest to the present invention are stent devices for holding open vascular lumens, such as veins or arteries, of a human patient.

A self-expanding stent device of interest to the present invention is compacted into a reduced profile delivery configuration and mounted about an inner catheter. The stent device is made of a shape memory material and will maintain its reduced profile configuration when below a transition temperature. Once the transition temperature is breached, the stent device will tend to return to its expanded profile, deployed configuration for holding open the bodily lumen. An outer sheath is provided to maintain the stent device in the reduced profile configuration even when the transition temperature is breached until the stent device is at a target treatment site. The delivery device is threaded through the passageways of the vasculature system to arrive the stent device at the treatment site. A guide wire is used, which extends through a lumen in the inner catheter, to guide the delivery device as appropriate. At the treatment site, the outer sheath is retracted to release the stent device to expand to the deployed configuration.

Generally, the inner catheter is provided with an anchor means to axially hold the stent device to the inner catheter as the outer sheath is retracted.

One known type of anchor means is a proximal stop abutting a proximal end of a stent device, as discussed with respect to FIGS. 1 and 2 in WO 00/71058. There is friction between an outer sheath and a stent device as the outer sheath is dragged over the outer surface of the stent device during retraction for deployment. Without the proximal stop, this friction would tend to move the stent device with the outer sheath. So that the stent device can be released, the proximal stop holds the stent device axially to the inner catheter and the outer sheath moves over the stent device. With this proximal stop arrangement, the friction tends to foreshorten the stent device, which compromises deployment accuracy. Furthermore, the total force on the proximal end of the stent device could damage the structure of the stent device, particularly as longer stent devices are used.

One alternative anchor means has been disclosed in WO 00/71058 whereby a surface element is fixed to an inner catheter and arranged to engage an inner surface of the stent device. One form for the surface element is a high friction sleeve extending continuously the full length of the stent device. The high friction sleeve holds the stent device axially to the inner catheter in a manner so that the force induced between the stent device and the inner catheter by the outer sheath dragging over the stent device during deployment is evenly distributed. The engagement between the sleeve and the inner surface of the stent device also forces the stout device into the outer sheath, which increases the overall deployment force as the outer sheath more strongly drags over the stent device. The degree of deployment force will increase with radial resiliency of the sleeve pushing the stent device radially into the outer sheath.

Another alternative disclosed in WO 00/71058 is to have axially spaced radial protuberances distributed along the length of, and engaging the inner surface of, the stent device. The reduced contact area between the stunt device and the radial protuberances, as compared to a continuous sleeve, reduces the overall deployment force, while at the same time distributing the force between the inner surface of the stent device and the inner catheter.

WO 2004/096091 discloses an inner catheter disposed radially within the lumen of the stent device having a spiral wire mounted thereabout. The spiral wire provides protrusions for engaging an inner surface of the stent device to hold the stent device axially as the outer sheath is retracted axially to release the stent device.

There is still a need in the art to reduce the deployment force in retracting an outer sheath to release a stent device, particularly with longer stent devices, while at the same time ensuring deployment accuracy. One object of the present invention is to meet this need.

SUMMARY OF THE INVENTION

The present invention provides:

A delivery device for delivering a stent device to a target treatment site, comprising:

- a stent device having a longitudinal axis, a lumen extending axially through the stent device, an inner surface defining the lumen and an outer surface, wherein the stent device is in a radially reduced profile, delivery configuration and is expandable to a radially increased profile, deployed configuration;
- an inner member extending axially through the lumen of the stent device;
- an outer sheath holding the stent device in the delivery configuration and axially retractable to release the stent device to expand to the deployed configuration; and
- anchorage configured to hold the stent device axially to the inner member as the outer sheath is dragged over an outer surface of the stent device;

characterised by the anchorage being such that a distal axial portion of the stent device is held to the inner member to a greater extent than the remaining axial length of the stent device.

The remaining portion of the stent device is thus more able to move with the outer sheath than the distal portion during retraction of the outer sheath. Thus, the remaining portion of the stent device may be arranged to move with the outer sheath relative to the relatively stationary distal portion. The portion of the outer sheath covering the distal portion of the stent device can, therefore, be retracted to a greater extent than the portion covering the remaining portion of the stent device. Accordingly, at the beginning of retraction of the outer sheath some, if not all, of the frictional forces associated with dragging the outer sheath over the remaining portion of the stent device can be foregone, with the limited frictional forces associated with dragging the outer sheath over the distal portion of the stent device contributing to the deployment force. The deployment force from stationary is thereby reduced. This is significant as stationary frictional forces between the outer sheath and the stent device are greater than dynamic frictional forces once the retraction has "got going". The reduction in deployment forces at the beginning is an important contribution to the art.

Further, as the anchorage of the remaining portion of the stent device to the inner member is of reduced holding force as compared to the distal portion, the deployment force during the remainder of retraction of the outer sheath can also be reduced.

Preferably, the anchorage is arranged so that the remaining portion of the stent device moves with the outer sheath relative to the distal portion of the stent device during retraction of the outer sheath.

Preferably, the anchorage comprises a stop for limiting axial movement of the stent device by abutting against a surface of the stent device, the stop spaced a predetermined axial distance from the surface so that the remaining portion of the stent device is able to move the predetermined distance with the outer sheath during retraction of the outer sheath.

The remaining portion of the stent device moves with the outer sheath and thus frictional movement does not take place therebetween. Thus, the deployment force is limited to that occurring as a result of friction at the distal portion of the stent device. Further, proximal movement of the stent device with the retracting outer sheath is restricted to a predetermined distance by a proximal stop so as to insure against damaging the stent device by over elongation.

Preferably, the stop is for abutting a proximal end surface of the stent device and is spaced proximally from the predetermined surface by the predetermined distance.

This arrangement of the stop allows a larger predetermined distance to be defined than if the stop was positioned axially within the stent device because the stent device will generally define a relatively compact structure.

Preferably, the anchorage comprises at least one protuberance extending radially from the inner member and engaging the inner surface of the stent device at the distal portion. Yet more preferably, the remaining portion of the stent device is free to move relative to the inner catheter. Further, the at least one protuberance preferably causes the stent device to protrude into the outer sheath and may cause the outer sheath to have a corresponding protrusion.

While in the prior art, protuberances extend radially from the inner member and are distributed the full length of the stent device, preferred embodiments of the present invention propose to provide at least one radial protuberance just at the distal portion, leaving the remaining portion free therefrom. In this way, the distal end of the stent device is appropriately positioned and the stent device is bulled out of the outer sheath from the front in a reduced deployment force manner.

Preferably, the at least one protuberance comprises a plurality of axially distributed protuberances. Preferably, the proximal most protuberance delineates the distal portion and the remaining portion of the stent device.

The protuberances may be provided by a continuous coil of material wrapped about the inner member. In this instance, each full circle around the inner member is considered as one protuberance.

Preferably, however, the at least one protuberance comprises a ring mounted on the inner member. Preferably, the at least one protuberance comprises two axially spaced rings, a distal most ring and a proximal most ring. Preferably, the distal most ring is positioned proximally of the end of the stent device.

The at least one protuberance is preferably made of a resilient material, which is deformed by the stent device. Preferably, the at least one protuberance is made of an adhesive material from which the stent device is able to expand in going from the delivery configuration to the deployed configuration.

A portion of the anchorage engages the inner surface of the stent device. In covered stent devices, the inner surface of the stent device frame is covered by a material for preventing or reducing cellular ingrowth obstructing the lumen of the stent device. An ePTFE layer is often provided as the cover material. In a bare stent device, the frame of the stent device is uncovered and defines the inner surface of the stent device. In the case of covered stent devices, a resilient material for engaging the inner surface is preferably used as part of the anchorage. That is, the protrusions or rings are preferably made of the resilient material described above. One example material is an adhesive selected from the range of medically approved Dymax adhesives. For bare stent devices, a metallic material engaging the inner surface of the stent device is preferably used as part of the anchorage. That is, the protuberances or rings are preferably metallic. These materials have been found to offer sufficient anchoring capability.

The present invention is suitably used with stent have a length greater than 60 mm, greater than 100 mm, greater than 150 mm, greater than 170 mm or even greater than 200 mm. As explained above, it is with the longer stents that deployment forces can be undesirably great. Further, longer stents provide scope for longer movement of the remaining portion of the stent device with the outer sheath without compromising the integrity of the stent device. For this reason also, the distal portion of the stent device is within an end 35% of the stent device, an end 30% of the stent device, an end 25% of the stent device, an end 20% of the stent device or even an end 15% of the stent device.

The present invention is considered useful for delivery device including a covered stent, but preferably the stent device is a bare stent. Problems of friction between the stent device and the outer sheath are particularly prevalent in such devices.

The stent device is preferably a self-expanding stent device of the known kind. Usually then, the stent device will be made of a shape memory material such as a shape memory alloy such as the commonly used nickel titanium alloy known as Nitinol.

The outer sheath is preferably made of a polymer material, which may stretch upon deployment force being applied to retract the outer sheath from the stent device. This stretching would be a hindrance with prior art anchorage arrangements because it would cause radial contraction of the outer sheath onto the stent device, thereby tightening the grip on the stent device and correspondingly increasing the deployment force. In preferred anchorage arrangements of the present invention, however, a space is provided radially between the remaining portion of the stent device and the inner member and extending axially the length of the stent device. This allows the stent device to contract with the outer sheath as well as move axially therewith so as to provide a limited contribution to frictional movement between the stent device and the outer sheath, thereby reducing deployment force.

A preferred embodiment of the present invention is given below with reference to the figures.

BRIEF DESCRIPTION OF THE FIGURE

FIG. 1 shows a delivery device of a preferred embodiment of the present invention for delivering a stent device in a reduced profiled delivery configuration. A distal region of the stent device is axially anchored to an inner catheter by annular rings about the inner catheter. A remaining portion of the stent device is spaced radially from the inner catheter. A proximal stop is spaced from a proximal end of the stent device. The stent device is maintained in the reduced profile delivery configuration by a retractable outer sheath.

DETAILED DESCRIPTION OF A PREFERRED EMBODIMENT

FIG. 1 discloses a delivery device 12 for delivering a stent device 3 to a target treatment site. The stent device 3 is mounted onto an inner catheter 2 (inner member) that extends radially within and axially through the stent device 3. The inner catheter 2 has an inner lumen extending axially therethrough for passage of a guide wire (not shown). The stent device is held 3 in an axially compact, delivery configuration by an outer sheath 1 mounted radially over the stent device 3 and extending axially therealong. The delivery device has a tapered distal tip 8. An actuation system (not shown) is included at a proximal handle portion to actuate retraction of the outer sheath 1 from over the stent device 3 to release the stent device 3 to radially expand to a deployed configuration.

An anchorage is provided for holding the stent device 3 axially relative to the inner catheter 3 while the outer sheath 1 is axially retracted in order to release the stent device 3 to expand to a deployed configuration. The anchorage consists of two annular rings 5, 6 and a proximal stop 4 fixed axially to the inner catheter 2. The two annular rings 5, 6 are a distal most ring 5 and a proximal most ring 6, which are axially spaced apart and which protrude radially from the inner catheter 2 to engage with an inner surface of the stent device 3 at locations adjacent a distal end of the stent device 3. The rings 5, 6 provide resistance to a distal portion 9 of the stent device 3 moving relative to the inner catheter 2 as the outer sheath 3 drags over the stent device 3. The remaining portion 10 of the stent device 3 proximal of the proximal most ring 6 is unanchored to the inner catheter 2. Instead, a radial gap 11 is provided between an inner surface of the remaining portion 10 of the stent device 3 and the inner catheter 2. The radial gap 11 extends axially along the length of the remaining portion 10 of the stent device 3. A space 7 is positioned axially between the proximal stop 4 and a proximal end of the stent device 3. The remaining portion 10 is thus free to move with the outer sheath 1 during retraction of the outer sheath 1 until it is stopped by abutment of the proximal end of the stent device 3 and the proximal stop 4. Simultaneously, the rings 5, 6 prevent axial movement of the distal portion 9 of the stent device 3 relative to the inner catheter 2 so that the outer sheath 1 moves proximally relative to the stent device 3 to begin retraction.

An exemplary delivery device has an outer sheath 1 made of (at least along the stent device) a polyether block amide with a hardness of 63 Shore D. Such an outer sheath 1 will have some stretch and radial compaction during retraction causing the remaining portion 10 of the stent device 3 to similarly radially compact towards the inner catheter 2 while moving axially with the outer sheath 1. While the proximal ring 6 will be put under radial stress by the compaction of the outer sheath 1, the distal ring will not be as the distal portion 9 of the outer sheath 1 does not compact and stretch. This contributes to reducing deployment force.

The preferred stent devices are relatively long in order that enough combined movement of the sheath 1 and the remaining portion 10 of the stent device 3 is allowed to properly effect initiation of retraction of the outer sheath at the distal portion 9. An exemplary delivery device 12 is 6 French (2 mm in diameter) with a length of the stent device of 175 mm. The axial space 7 between a proximal end of the stent device 3 and the proximal stop 4 for such a delivery device 12 is 3 mm, which is large enough to initiate retraction of the outer sheath 1, but not so large as to jeopardise the integrity of the stent device 3. The first ring 5 is placed 10 mm proximal of the distal end of the stent device 3 and the second ring is placed 30 mm proximal of the distal end of the stent device 3. This is considered an acceptable distribution to hold the distal end for enough of the retraction of the outer sheath 1 to sufficiently support the stent device 3 during initiation of retraction, while at the same time providing a sufficiently large remaining portion 20 for reducing deployment force.

The stent device 3 is a bare stent of the self-expanding variety. An exemplary self expanding material for the stent device 3 to be made of is Nitinol. The stent device 3 is made up of a number of stenting rings formed of zigzagging strut members. Adjacent stenting rings are joined by one or more bridging struts.

An exemplary material for the rings 5, 6 is a cyanoacrylate medical adhesive that is soft enough to provide a cushion that is radially deformed by the stent device 3. The rings 5, 6 resiliently force the stent device 3 into the outer sheath 1 to the extent of causing the outer sheath 3 to protrude where the rings 5, 6 are located by an amount of approximately 0.05 mm. The adhesive rings 5, 6 are also adhered to the inner surface of the stent device 3 in such a way as to provide a strong engagement with the stent device 3 to resist the stent device 3 moving with the outer sheath 1 during retraction, while at the same time allowing the stent device 3 to radially expand upon being released by the outer sheath 1.

A method of use of the delivery device 12 will now be described. The delivery device is threaded through a path in a vasculature system in order to position the stent device 3 at the target treatment site. The path is defined by a guide wire, which passes through the inner catheter 2 as the delivery device 12 is moved. The appropriate position of the stent device 3 is determined with the use of radiopaque markers (not shown) mounted to the delivery device 12. Once correctly positioned, an actuation mechanism at a proximal handle will be operated to cause the outer sheath 1 to be pulled proximally while the inner catheter 2, and thus the stent device 3, is held stationary.

The position of the stent device 3 at the distal portion is held fixed to the inner catheter 2 by the rings 5, 6. The outer sheath 1 moves proximally, which will cause the remaining portion 10 of the stent device 3 to at least partially move with the outer sheath 1 until it abuts against the proximal stop 4. Frictional force between the outer sheath 1 and the remaining portion 10 of the stent device 3 is thus limited. The outer sheath 1 does, however, move proximally relative to the stent device 3 at the distal portion 9 because the distal portion 9 of the stent device 3 is held fixed to the inner catheter 2 by the rings 5, 6. Retraction of the outer sheath 1 is thereby initiated.

The rings 5, 6 structurally support the stent device 3 at the beginning of retraction, which is when resistance to the outer sheath 1 moving relative to the stent device is relatively high. Portions of the stent device 3 that are released expand to the deployed configuration to support the bodily lumen. Retraction of the outer sheath 1 continues until the outer sheath 1 moves proximally past the rings 5, 6. At this stage, the unexpanded stent device 3 is unsupported by further engagement between the inner surface of the stent device 3 and the inner catheter 2. Instead, proximal movement of the stent device 3 with the outer sheath 1 is prevented by the proximal end of the stent device 3 abutting the proximal stop 4. Resistance to movement of the outer sheath 1 relative to the stent device 3 is of a limited amount now that the stent device 3 is partially deployed and the initial retraction force has been overcome. It is dynamic friction, as opposed to static friction, between the outer sheath 1 and the outer surface of the stent device 3 that exists. Accordingly, the overall axial force put on the stent device 3, even with the use of a proximal stop 4, is modest and does not risk damaging the stent device 3. Proximal movement of the outer sheath 1 continues until the entire stent device 3 is released and the stent device 3 is deployed.

The presently preferred embodiment of the invention has been described above with reference to FIG. 1. The skilled person will envision alternative embodiments that fall within the scope of the claims. Some alternative embodiments falling within the invention that may be useful are given below.

The anchor means of the invention could be made up of a coil of resilient material wrapped around the inner member. The coil would extend along the inner member at the distal end and engage the inner surface of the stent device to define the distal portion. Adjacent turns of the coil provide axially adjacent protrusions engaging the inner surface of the stent device. The stent device would radially deform the coil, which could be made of a deformable polymer, perhaps the adhesive material discussed above. The axial density of the coil turns could be adjusted depending on how much engagement between the stent device and the inner member is wanted and how much frictional force between the outer sheath and the stent device, as caused by the resiliency of the material of the coil, could be tolerated.

The anchor means engaging the inner surface of the stent device could be provided by a layer of material coated on the inner member and extending the full length of the stent device. The layer of material could be made of a high friction material along the distal portion of the stent device and a low friction material along the remaining portion of the stent device. In this way, the stent device is able to slip relative to the inner member at the remaining portion and the distal portion would be held fixed to the inner member, thereby providing the effects of the invention described above.

In another envisaged alternative, the anchor means could include protrusions on the inner member that extend through the thickness of the stent device at the distal portion. Such protrusions would engage a radially extending surface of the stent device, thereby preventing the stent device from moving axially relative to the inner member at the distal portion.

Such alternatives and others occurring to the skilled person are intended to fall within the scope of the claims.

The invention claimed is:

1. A delivery device for delivering a stent device to a target treatment site, comprising:
    a stent device having a longitudinal axis, a lumen extending axially through the stent device, an inner surface defining the lumen and an outer surface, wherein the stent device is in a radially reduced profile, delivery configuration and is expandable to a radially increased profile, deployed configuration;
    an inner member extending axially through the lumen of the stent device;
    an outer sheath holding the stent device in the delivery configuration and axially retractable to release the stent device to expand to the deployed configuration; and
    anchorage configured to hold the stent device axially to the inner member as the outer sheath is dragged over an outer surface of the stent device;
    the anchorage being such that a distal axial portion of the stent device is held to the inner member to a greater extent than a remaining axial length of the stent device;
    the anchorage comprises a stop for limiting axial movement of the stent device by abutting against a surface of the stent device, the stop being spaced a predetermined axial distance from the surface so that the remaining portion of the stent device is able to move the predetermined distance with the outer sheath during retraction of the outer sheath,
    wherein the stop is arranged to abut a proximal end surface of the stent device and is spaced proximally from the surface by the predetermined distance.

2. The delivery device of claim 1, wherein the anchorage is arranged so that the remaining portion of the stent device moves with the outer sheath relative to the distal portion of the stent device during retraction of the outer sheath.

3. The delivery device of claim 1, wherein the anchorage comprises at least one protuberance extending radially from the inner member and engaging the inner surface of the stent device at the distal portion.

4. The delivery device of claim 3, wherein the at least one protuberance comprises a plurality of axially distributed protuberances.

5. The delivery device of claim 4, wherein a proximal most protuberance delineates the distal portion and the remaining portion of the stent device.

6. The delivery device of claim 5, wherein a distal most protuberance is positioned proximally of the distal end of the stent device by a predetermined distance.

7. The delivery device of claim 3, wherein the at least one protuberance comprises a ring mounted on the inner member.

8. The delivery device of claim 7, wherein the at least one protuberance comprises two axially spaced rings, a distal most ring and a proximal most ring.

9. The delivery device of claim 3, wherein the at least one protuberance is made of a resilient material, which is radially deformed by the stent device.

10. The delivery device of claim 3, wherein the at least one protuberance is made of an adhesive material, which the stent device is able to peel away from in going from the delivery configuration to the deployed configuration.

11. The delivery device of claim 1, wherein the anchorage is such that the remaining portion of the stent device is free to move relative to the inner member.

12. The delivery device of claim 1, wherein the stent device has an axial length greater than 60 mm.

13. The delivery device of claim 1, wherein the distal portion of the stent device is within an end 35% of the stent device.

14. The delivery device of claim 1, wherein the outer sheath stretches upon deployment force being applied to retract the outer sheath from the stent device.

15. The delivery device of claim 1, wherein a space is provided radially between the remaining portion of the stent device and the inner member and extending axially the length of the stent device.

16. The delivery device of claim 1, wherein the stent device has an axial length greater than 100 mm.

17. The delivery device of claim 1, wherein the stent device has an axial length greater than 150 mm.

18. The delivery device of claim 1, wherein the stent device has an axial length greater than 170 mm.

19. The delivery device of claim 1, wherein the stent device has an axial length greater than 200 mm.

20. A stent delivery device, comprising:
- a stent;
- an inner member extending axially through a lumen of the stent;
- an outer sheath holding the stent in a delivery configuration, the outer sheath axially retractable to release the stent to expand to a deployed configuration; and
- anchorage configured to hold the stent axially to the inner member as the outer sheath is retracted, the anchorage including:
  - structure to hold a distal portion of the stent to a greater extent than a remaining length of the stent proximal of the distal portion; and
  - a stop to limit axial movement of the stent by abutting against a proximal end of the stent, the stop spaced a predetermined distance from the stent proximal end to permit movement of the remaining length of the stent during retraction of the outer sheath.

* * * * *